United States Patent [19]

Imran

[11] Patent Number: 5,782,899
[45] Date of Patent: *Jul. 21, 1998

[54] ENDOCARDIAL MAPPING AND ABLATION SYSTEM UTILIZING A SEPARATELY CONTROLLED ABLATION CATHETER AND METHOD

[75] Inventor: Mir A. Imran, Palo Alto, Calif.

[73] Assignee: Cardiac Pathways Corporation, Sunnyvale, Calif.

[ * ] Notice: The term of this patent shall not extend beyond the expiration date of Pat. No. 5,324,284.

[21] Appl. No.: 697,632

[22] Filed: Aug. 28, 1996

Related U.S. Application Data

[63] Continuation of Ser. No. 439,663, May 11, 1995, Pat. No. 5,578,007, which is a continuation of Ser. No. 206,463, Mar. 4, 1994, abandoned, which is a division of Ser. No. 894,529, Jun. 5, 1992, Pat. No. 5,324,284.

[51] Int. Cl.$^6$ ............................................. A61B 5/04
[52] U.S. Cl. ..................... 607/122; 600/374; 606/41; 607/101
[58] Field of Search ....................... 607/100–102, 607/115, 116, 119, 122; 128/642; 606/41, 42, 45–50; 600/372–374

[56] References Cited

U.S. PATENT DOCUMENTS

| | | |
|---|---|---|
| 4,308,164 | 12/1981 | Hess . |
| 4,543,090 | 9/1985 | McCoy . |
| 4,699,147 | 10/1987 | Chilson et al. . |
| 4,758,222 | 7/1988 | McCoy . |
| 4,785,815 | 11/1988 | Cohen . |
| 4,928,689 | 5/1990 | Hauser . |
| 4,940,064 | 7/1990 | Desai ............................ 607/122 |
| 4,998,916 | 3/1991 | Hammerslag . |
| 5,152,748 | 10/1992 | Chastagner . |
| 5,156,151 | 10/1992 | Imran ............................ 128/642 |
| 5,330,466 | 7/1994 | Imran . |
| 5,409,000 | 4/1995 | Imran ............................ 128/642 |
| 5,415,166 | 5/1995 | Imran ............................ 128/642 |
| 5,476,495 | 12/1995 | Kordis et al. . |
| 5,487,385 | 1/1996 | Avitall ............................ 128/642 |
| 5,500,012 | 3/1996 | Brucker et al. ............... 607/122 |
| 5,595,183 | 1/1997 | Swanson et al. ............. 607/122 |

*Primary Examiner*—Michael Peffley
*Attorney, Agent, or Firm*—Flehr Hohbach Test Albritton & Herbert LLP

[57] ABSTRACT

Endocardial mapping and ablation system for introduction into a chamber of a heart formed by a wall and having a passage leading thereto. The system is comprised of a catheter probe having a distal extremity. A plurality of electrodes are carried by the distal extremity for mapping the wall of the chamber. An ablation catheter is provided having a distal extremity. The ablation catheter has control capabilities whereby the distal extremity can be bent separately of movement of the catheter probe to come into close proximity to the wall of the heart. The distal extremity of the ablation catheter is provided with capabilities for ablating a portion of the wall of the heart to eliminate an arrythmia in the heart.

4 Claims, 1 Drawing Sheet

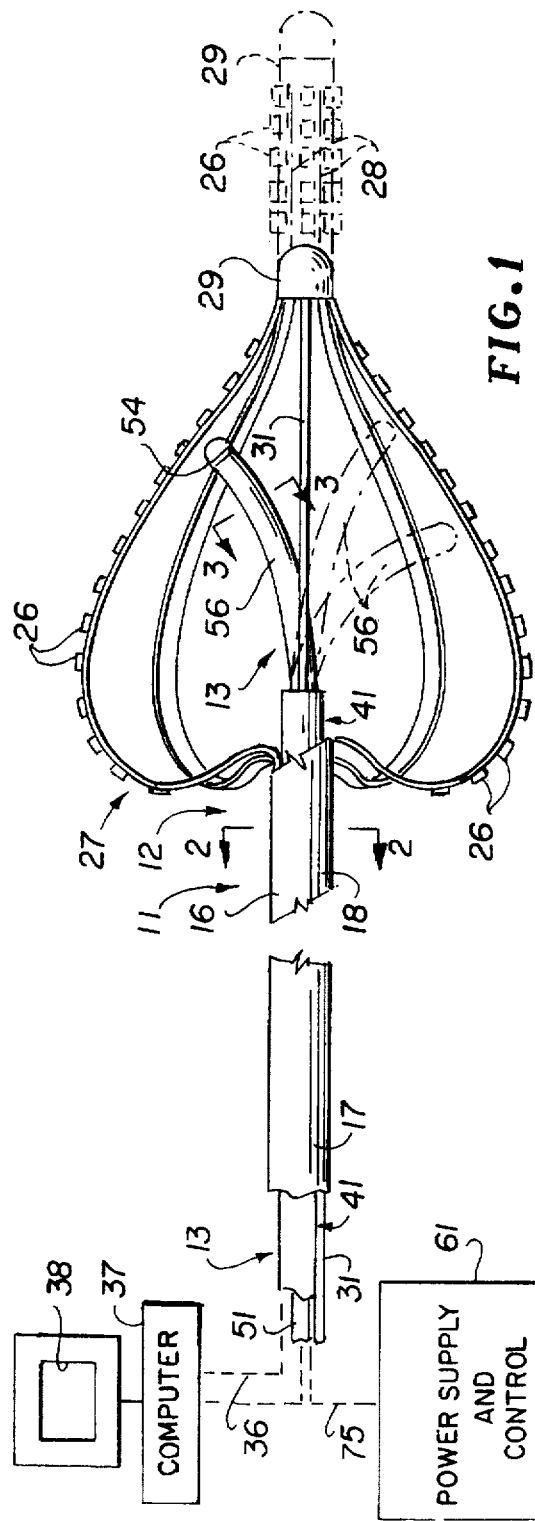
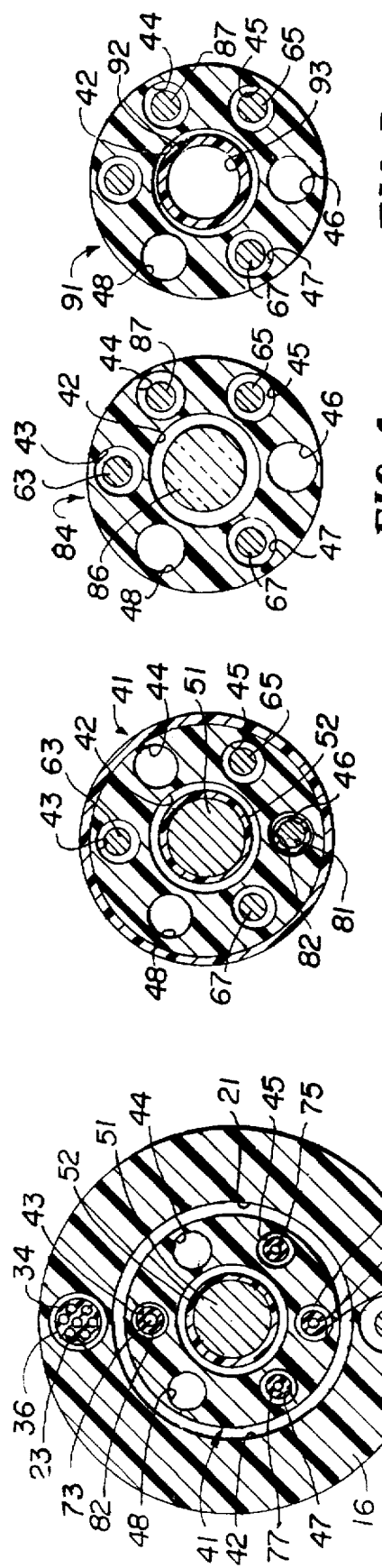

1

ENDOCARDIAL MAPPING AND ABLATION SYSTEM UTILIZING A SEPARATELY CONTROLLED ABLATION CATHETER AND METHOD

This is a continuation of application Ser. No. 08/439,663 filed May 11, 1995, now U.S. Pat. No. 5,578,007, which is a continuation of application Ser. No. 08/206,463 filed Mar. 4, 1994, abandoned, which is a division of application Ser. No. 07/894,529 filed Jun. 5, 1992, now U.S. Pat. No. 5,324,284.

This invention relates to an endocardial mapping and ablation system utilizing a separately controlled ablation catheter.

In co-pending application Ser. No. 07/656,764 filed Feb. 15, 1991 now U.S. Pat. No. 5,156,161, there is disclosed an endocardial mapping and/or ablation system which includes a plurality of longitudinally and radially spaced apart electrodes which are utilized for mapping and also which can be utilized for ablation. However, a need has arisen whereby it is desirable to be able to provide ablation which is independent of the electrodes carried by the mapping and or ablation system. There is therefore a need for a new and improved endocardial mapping and/or ablation system which overcomes this disadvantage.

In general, it is an object of the present invention to provide an endocardial mapping and ablation system and method which utilizes a separately controlled ablation catheter.

Another object of the invention is to provide a system, catheter and method of the above character in which the distal extremity of the ablation catheter can be independently controlled.

Another object of the invention is to provide a system, catheter and method of the above character in which once the site where the arrythmia originates has been located, the ablation catheter can be steered separately to that location to perform an ablation.

Another object of the invention is to provide a system, catheter and method of the above character in which radio frequency energy can be delivered to perform the ablation.

Another object of the invention is to provide a system, catheter and method of the above character in which laser energy can be delivered to perform the ablation.

Another object of the invention is to provide a system, catheter and method of the above character which can be utilized for delivering pulse laser energy for performing the ablation.

Another object of the invention is to provide a system, catheter and method of the above character which includes a cannula for delivering a chemical into the heart muscle to perform the desired ablation.

Another object of the invention is to provide a system, catheter and method of the above character in which ablation can be accomplished without interfering with an electrocardiogram.

Additional objects and features of the invention will appear from the following description in which the preferred embodiments are set forth in detail in conjunction with the accompanying drawings.

FIG. 1 is a side elevational view of an endocardial mapping and ablation system utilizing a separately controlled ablation catheter incorporating the present invention.

FIG. 2 is a cross-sectional view taken along the line 2—2 of FIG. 1.

FIG. 3 is a cross-sectional view taken along the line 3—3 of FIG. 1.

FIG. 4 is a cross-sectional view similar to FIG. 3 showing the use of an ablation catheter which has a capability of delivering pulsed laser energy for ablation.

FIG. 5 is a cross-sectional view also similar to FIG. 3 which shows the use of a retractable cannula for delivery of a chemical for ablation.

In general, the endocardial mapping and ablation system with a separately controlled ablation catheter is for introduction into a chamber of the heart of a patient with the heart being formed by a wall and with the heart having a passage leading to the chamber. A catheter probe is provided which has proximal and distal extremities. A plurality of electrodes are carried by the distal extremity of the catheter probe for mapping the wall of the chamber. An ablation catheter is provided with its distal extremity being disposed in the distal extremity of the catheter probe. Control means is provided for the ablation catheter whereby the distal extremity can be moved independently and separately of movement of the catheter probe to move the distal extremity into close proximity to the wall of the heart. Means is carried by the distal extremity of the ablation catheter for performing an ablation operation in the desired location in the wall of the heart.

More in particular, the mapping and ablation system 11 of the present invention consists of a catheter probe 12 and an ablation catheter 13. The catheter probe 12 is described in detail in co-pending application Ser. No. 07/656,764 filed Feb. 15, 1991 now U.S. Pat. No. 5,156,161. As described therein, it is comprised of a flexible elongate member 16 formed of a suitable material such as plastic which is provided with proximal and distal extremities 17 and 18. The flexible elongate member 16 is provided with a centrally disposed lumen 21 extending the length thereof. It should be appreciated that although the lumen 21 is shown as being centrally disposed, it can be offset if desired. Also, it is provided with a plurality of additional lumens such as lumens 22 and 23, which also extend the length of the flexible elongate member 16. If desired, still further additional lumens can be provided. As described in said co-pending application Ser. No. 07/656,764 filed Feb. 15, 1991, now U.S. Pat. No. 5,156,161 the catheter probe 12 includes a plurality of longitudinally and radially spaced apart electrodes 26. Expandable means 27 is secured to the distal extremity of the flexible elongate member 16 for mounting the electrodes 26. The expandable means 27 as shown is formed of a plurality of flexible arms 28 which are movable between a contracted position and an expanded position. The proximal extremities of the arms 28 are secured to the distal extremity of the flexible elongate member 16. The distal extremities of the arms 16 are secured within a cylindrical tip 29 which is provided with a rounded or hemispherical distal extremity.

Means is provided for moving the expandable means 27 between expanded and contracted positions and consists of a pull wire 31 which has its distal extremity secured within the cylindrical tip 29 and which extends between the arms 28 through the lumen 22 of the flexible elongate member 16, out the distal extremity of the member 16. This permits manual operation of the pull wire 31 exterior of the human body containing the heart. The movement of the distal extremity of the expandable means 27 in moving from an expanded position to a contracted dotted-line position is shown in FIG. 1. It can be seen that by pulling on the pull wire 31, the tip 29 is pulled rearwardly or to the left as viewed in FIG. 1 to cause expansion of the expandable means whereby pushing of the pull wire 31 forwardly or to the right as viewed in FIG. 1 will cause contraction of the same.

The electrodes 26 are connected to conductors 34 provided in a cable 36 which extends through the lumen 23 of the flexible elongate member 16. The cable 36 is connected to a computer 37 which is provided with a video screen 38.

The ablation catheter 13 is a separate component and is slidably mounted in the lumen 21 of the flexible elongate member 16 of the catheter probe 12. Alternatively, it can be positioned independently of the catheter probe 12 along side the catheter probe 12. The ablation catheter 13 is comprised of a flexible elongate member 41 formed of a suitable material such as a medical grade plastic. It is provided with a centrally disposed or larger lumen 42 and six additional lumens 43–48 which are generally equally circumferentially spaced around the central lumen 42. The lumens 43, 45 and 47 are offset by approximately 120° with respect to each other. A conductor 51 of a suitable conducting material such as copper and covered by an insulating layer 52 is disposed in the central lumen 42 and, when RF energy is used for ablation, is connected to a hemispheric electrode 54 mounted on the tip or distal extremity 56 of the flexible elongate member 41. This same conductor can also be utilized for sensing for an electrocardiogram. This conductor 51 can also serve as a stiffening element for the flexible elongate member 41, if that is desired.

The flexible elongate member 41 is provided with a proximal extremity through which the conductor 51 extends, which can be connected to the computer 37 and, alternatively or in addition, to a power supply and control console 61 as shown by the dotted lines.

Means is provided for causing bending movement of the distal extremity of the flexible elongate member 41 and consists of flexible elongate elements 63, 65 and 67 which are disposed in the lumens 43, 45 and 47. These flexible elongate elements are formed of a material having a negative coefficient of expansion and are of the type described in co-pending application Ser. No. 07/793,858 filed Nov. 18, 1991 now U.S. Pat. No. 5,258,005. As described therein, one material suitable for this purpose is a nickel titanium alloy manufactured and sold under the trademark Flexinol by Toki of Japan. As explained in said co-pending application, the heating of the Flexinol wire changes its crystalline structure causing it to shorten itself, or in other words to have a negative coefficient of expansion upon the application of heat to the same. These elements 63, 65 and 67 can be heated by passing electrical current therethrough. This is accomplished by the use of three separate conductors 73, 75 and 77 which are bonded to the proximal extremities of the flexible elongate elements 63, 65 and 67 in the manner described in co-pending application Ser. No. 07/793,858 filed Nov. 18, 1991. The conductors 73, 75 and 77 are provided with insulation 78 and are disposed in the lumens 43, 45 and 47. All of them are connected to the power supply and control console 61.

The distal extremities of the flexible elongate elements 63, 65 and 67 are bonded together in a suitable manner and are connected to a ground conductor 81 having insulation 82 thereon. The conductor 81 is disposed in the lumen 46 and extends the length thereof. It is also connected to the power supply and control console 61 to provide a ground return for the flexible elongate elements 63, 65 and 67.

Operation and use of the endocardial mapping and ablation system utilizing a separately controlled ablation catheter and the method of using the same may be briefly described as follows. The system is used in a conventional manner as described in co-pending application Ser. No. 07/656,764 filed Feb. 15, 1991 now U.S. Pat. No. 5,156,161. The catheter probe 12 can be introduced through the superior or inferior vena cavae into the right atrium and then advanced into the right ventricle, assuming that is the desired cavity of the heart (not shown) or into the left ventricle via the aorta. The cavity is formed by a wall of the heart and has a passage leading thereto as hereinbefore described. The pull wire 31 is then pulled to cause the expandable means 27 with the electrodes 26 carried thereby to be moved into engagement with the wall of the heart. The computer 37 is then utilized to map the various potentials within the wall forming the cavity of the heart and an isochronal map thereof is displayed on the computer screen 38. As soon as the focus of the arrythmia has been located, the user, i.e. the physician, identifies the particular electrode of the electrodes 26 where ablation energy is to be delivered. Rather than delivering ablation energy through the selected electrode 26, ablation is achieved in the present invention by the use of the separately controlled ablation catheter 13.

The ablation catheter 13 is advanced through the lumen 21 by visualizing the same, as for example by visualizing the tip electrode 54 with x-rays. It should be appreciated that if desired, additional markers can be provided on the tip if necessary to provide adequate visualization with x-rays. As the ablation catheter 13 is being advanced into the chamber of the heart and into the expandable means 27, it can be bent in the desired direction by the use of the control console 61 which is of the type described in co-pending application Ser. No. 07/793,858 filed Nov. 18, 1991, now U.S. Pat. No. 5,258,005. Operation of the control console 61 causes heating of the appropriate Flexinol wires 63, 65 and 67 to cause bending of the distal extremity 56 of the flexible elongate member 41 in the desired direction until the portion of the wall of the heart which is to be ablated is approached so that it is in close proximity or in contact therewith. Typically the electrode 54 will be generally flush with the arm 28 which carries the electrode 26 in the closest proximity to the region to be ablated. As soon as the ablation catheter 13 has been manipulated so that the electrode 54 is in the desired position, ablation energy is caused to be delivered through the ablation conductor 51 to the electrode 54 and through the return ground conductor to create an ablation in the tissue of the wall of the heart which is the focus of the arrythmia. By this ablation, the arrythmia should be eliminated. Thereafter the ablation catheter 13 and the catheter probe 12 can be removed.

It should be appreciated that the distal extremity 56 of the ablation catheter can be bent in various directions extending about 3600 of the longitudinal axis of the ablation catheter 13. In this way, it is possible for the distal extremity 56 of the separately controlled ablation catheter 13 to be moved into contact with any portion of the wall of the heart in the chamber in which the catheter probe 12 is disposed and contacted by one of the electrodes 26.

It should be appreciated that the computer 37 can be utilized for automatically positioning the distal extremity of the ablation catheter 13. The computer collects the information from the electrodes 26 and the expandable means 27 and displays them on the isochronal map on the computer screen 38 of the wall of the chamber of the heart in which the expandable means 27 is disposed. The physician utilizing the isochronal map identifies the particular electrode where ablation energy is to be delivered. The computer 37 operates with the power supply 61 to manipulate the distal extremity of the ablation catheter to bring the distal extremity adjacent to the electrode selected by the physician. Once the distal extremity of the ablation catheter 13 is near the electrode selected by the physician, the computer starts matching the electrocardiogram signal picked up from the tip of the ablation catheter 13 and the electrode selected on the expandable means 27. Once a match is achieved, radiofrequency ablation energy is delivered from the power supply 61 to the electrode 54 to cause the desired ablation to occur. After the ablation has been performed, the ablation catheter 13 and the catheter probe can be removed.

One of the principal advantages of utilizing a separately controlled ablation catheter 13 is that means other than RF energy can be utilized for performing an ablation. For example, as shown in FIG. 4, in place of the center conductor 51, a fiber optic 86 can be provided which extends through the lumen 42 with the lumen 42 extending through the distal extremity of the flexible elongate member 41 to permit pulsed laser energy to be delivered to the ablation site. By way of example, pulsed laser energy can be delivered from an excimer laser through pure silica fibers serving as the fiber optic 86 to deliver such pulsed energy to the ablation site. In such an arrangement, it may be desirable to place another conductor 87 in the lumen 44 which can serve as a conductor to an ECG sensing electrode which can be connected into the computer 37.

Another alternative for delivering ablation means to the wall of the heart is shown in FIG. 5 and consists of an ablation catheter 91 in which a retractable cannula 92 is disposed in the lumen 42. The retractable cannula can be of the type described in co-pending application Ser. No. 07/656,764 filed Feb. 15, 1991, now U.S. Pat. No. 5,156,161. The cannula 92 can be advanced under the control of the control console 61 and, after an appropriate incision has been made into the tissue of the wall of the heart, a chemical can be introduced into the incision by utilizing the centrally disposed lumen 93 provided centrally within the cannula 92. A controlled amount of the chemical can be delivered to the desired site to cause the desired amount of ablation of tissue of the heart.

The means for ablation provided in FIGS. 4 and 5 has an advantage over the RF energy which is delivered in the embodiment shown in FIGS. 1, 2 and 3 because it makes it possible to observe the electrogram on the screen 38 during the time that the ablation is taking place, and to thereby ascertain when the arrythmia disappears. This is generally not possible when radio frequency energy is used for ablation because the radio frequency interferes with the electrocardiogram being produced, so that it is difficult, if not impossible, to observe the same on the screen 38. Thus it can be seen that there is a distinct advantage in using means other than RF energy for causing ablation in the wall of the heart.

In view of the foregoing, it can be seen that there has been provided an endocardial mapping and ablation system utilizing a separately controlled ablation catheter which facilitates performing precise ablations after the mapping operation has been completed. By the use of chemicals and/or laser energy, it is possible to perform such ablations while observing the electrocardiogram, thereby giving the physician the opportunity to ascertain when ablation should be discontinued by noticing the disappearance of the arrythmia.

What is claimed is:

1. A catheter system for mapping and ablation within a chamber of the heart formed by a wall having an inner surface comprising a plurality of flexible arms and an ablation electrode positioned within the chamber, said flexible arms having distal extremities and connected at the distal extremities to form a basket configuration, each of said arms including a plurality of mapping electrodes, said arms being expandable into contact with the inner surface to facilitate mapping, said ablation electrode including a support for carrying said ablation electrode and for adjusting the position of the ablation electrode independently of the flexible arms to bring the ablation electrode into engagement with the inner surface while maintaining the flexible arms of the basket in engagement with the inner surface.

2. A catheter system as in claim 1 wherein said support is in the form of a separate catheter movable independently of the flexible arms of the basket.

3. A method for endocardial mapping and ablation utilizing a catheter system for introduction into a chamber of a heart formed by a wall having an inner surface, said catheter system including an expandable basket with a plurality of arms, each arm carrying a plurality of mapping electrodes, said catheter system further including at least one ablation electrode, the method comprising the steps of expanding the basket so that the arms come into contact with the inner surface, performing a mapping operation using the mapping electrodes carried on the arms, independently moving the ablation electrode to a desired location on the inner surface while maintaining the position of the arms of the basket and ablating the wall having the inner surface using the ablation electrode.

4. A method for endocardial mapping and ablation of the wall of the heart forming a chamber therein and having a passage leading thereto by utilization of a catheter probe including an expandable basket with a plurality of arms having a plurality of mapping electrodes carried by the plurality of arms and an ablation catheter, introducing the catheter probe into the chamber of the heart, performing mapping operations with the catheter probe by expanding the expandable basket to bring the mapping electrodes of the catheter probe into engagement with the wall of the heart in spaced-apart positions to ascertain the focus of an arrhythmia in the heart, thereafter independently manipulating the distal extremity of the ablation catheter while the mapping electrodes are in the chamber of the heart so that the distal extremity of the ablation catheter is brought into close proximity to the focus of the arrhythmia and utilizing the ablation catheter for ablating tissue of the wall of the heart.

* * * * *